US005618841A

United States Patent [19]

Kross

[11] Patent Number: 5,618,841

[45] Date of Patent: Apr. 8, 1997

[54] COMPOSITION OF IODOPHOR TEAT DIP FOR THE PREVENTION OF MASTITIS AND A PROCESS FOR USING THE SAME

[76] Inventor: Robert Kross, 2506 Florin Ct., Bellmore, N.Y. 11710

[21] Appl. No.: 271,374

[22] Filed: Jul. 6, 1994

[51] Int. Cl.[6] ........................ A61K 31/19

[52] U.S. Cl. ........................ 514/557; 514/560

[58] Field of Search ........................ 514/557, 560

[56] References Cited

U.S. PATENT DOCUMENTS 4,844,898 7/1989 Komori et al. ........................ 424/150

*Primary Examiner*—José G. Dees
*Assistant Examiner*—Joseph M. Conrad, III
*Attorney, Agent, or Firm*—Edwin D. Schindler

[57] ABSTRACT

A composition for improving the anti-microbial activity of mammalian iodophor teat dips is disclosed, which includes an iodophor concentrate an organic acid buffer having an antimicrobial acid within the pKa range of from approximately 2.0 to 6.0, preferably within the pKa range of from approximately 3.0 to 5.0. Antimicrobial acids for use as the organic acid buffer include lactic acid, malic acid, mandelic acid, formic acid, glycolic acid, benzoic acid and combinations thereof.

2 Claims, No Drawings

COMPOSITION OF IODOPHOR TEAT DIP FOR THE PREVENTION OF MASTITIS AND A PROCESS FOR USING THE SAME

BACKGROUND OF THE INVENTION

1. Technical Field of the Invention

The present invention relates, generally, to a composition, and method of use therefor, of iodophor teat dips for the prevention of bacterial infections in a mammal's udder. More particularly, the present invention relates to the prevention of bovine mastitis through the use of antimicrobial buffering agents for iodophor teat dip disinfectants.

2. Description of the Prior Art

As a result of selective breeding, man has produced dairy cattle having mammary glands with a milk-secreting potential far in excess of the requirements of the newborn calf. Because of the size, position and anatomic adjustment for rapid removal of large volumes of milk, the udders of present diary cows are especially prone to injury and infection. The resulting inflammation is called mastitis, which causes an estimated $2 billion annual loss in U.S. milk production.

Faulty managerial practices can control both sources of mastitis, trauma and bacterial infection. In the latter regard, experience has indicated that its frequency among cows in a herd, and the intensity of infections may be lessened by proper use of antimicrobial materials. These antimicrobials take the form of pre-milking teat-washing sanitizers and have been modified in recent years through inclusion of polymeric materials which deposit a film barrier over the surface of the teat, for helping to minimize transfer of residual and/or newly-deposited microorganisms into the teat interior.

It has been estimated that more than half the cows the United States have some type of mastitis, which are classified into two forms. These are "clinical," characterized by detectable changes in milk and gland, and "sub-clinical," where the infection is not directly evident. Microscopic examination of milk from sub-clinically-mastitic cows shows increased levels of white cells and often the causative bacteria. Most mastitis infections are in the latter category. "Contagious" mastitis, caused by the microorganisms *Strep, agalactiae* and *Staph, aureus,* is associated with infections which arise primarily by the transfer of these microorganisms from one cow to the next by contamination of milking equipment and milkers'hands during the milking procedure.

A broader range of organisms are associated with "environmental" mastitis. This derives from the contamination of the cow's udder by microorganisms which contact the teat between milkings, such as from wind-borne matter, bedding material and other ground contaminants (e.g., soil, manure) that contact the gland when the animal lies down. Environmental organisms include the coliforms, *Escherichia coli, Klebsiella pneumoniae,* Enterobacter spp. and Citrobacter spp., as well as *Strep. uberis, Strep. dysgalactiae,* and *Pseudomonas aeruginosa.*

The pre- and post-milking teat dips, including the barrier formers, generally contain antimicrobials of the following classes: iodophors, quaternary ammonium compounds, chlorhexidine, sodium hypochlorite, hydrogen peroxide, organic acids (e.g., lactic, lauric), dodecylbenzene sulfonic acid, chlorous acid and bacteriocins. Many of these are very effective in destroying mastitis-causing organisms upon contact and, thus, are effective in protecting against contagious mastitis, but have limited effectiveness in preventing against environmental mastitis. During the 8–12 hour intermilking period, insufficient amounts of these antimicrobias remain to destroy invading microorganisms. Even barrier-forming teat dips, and iodophor test dips, which deposit free iodine that is substantive to skin tissue, still leave large numbers of cows susceptible to mastitis caused by environmental microorganisms.

The search has continued for a means for extending the protective effects of current teat dip technologies, to further minimize the incidence of environmental mastitis. The present invention, a result of experimental studies designed to meet this need, is the discovery of a procedure for augmenting the antimicrobial activity associated with iodophor teat dips. The present invention, an improved disinfection system, can be applied to standard antimicrobial teat dips or to the newly-emerging, barrier-forming polymer compositions in order to further expand the protection afforded by antimicrobial iodophor teat dips against environmental mastitis.

SUMMARY OF THE INVENTION

It is, therefore, an object of the present invention to provide a composition and a process for improving the antimicrobial activity of bovine iodophor teat dips and, thus, increase the protection they afford during the period of time between milkings.

It is a further object of the present invention to replace the present buffering agents used for stabilizing iodophor teat dip compositions with buffering agents which are inherently also antimicrobial agents, which can therefore provide disinfection during the intermilking period.

An additional object of the presently claimed invention is to increase the protection offered by barrier teat dips by supplementing their physical protection with an antimicrobial activity greater than that provided by residues of the disinfecting teat dip applied shortly after milking.

It is, yet, a further object of the present invention to overcome and substantially alleviate the above-described disadvantages inherent in prior art procedures.

The foregoing and related objects are achieved by the present invention which provides, in one aspect, a method for augmenting the antimicrobial activity of iodophor teat dips through the use of antimicrobial organic acid buffers, wherein the acid strengths of the organic acids are such that their effective buffering ranges coincide with solutions having pH values which are appropriate for the stability and effectiveness of the iodophor compositions. The acids useful in carrying out the present invention fall within the pKa range of from 2.0 to 6.0, with a preferred range of 3.0 to 5.0. Suitably, effective antimicrobial acids in this preferred range are lactic, malic, mandelic, formic, glycolic and benzoic acids.

In another aspect of the invention, the claimed invention provides a composition which extends the antimicrobial time duration of iodophor teat dips to kill environmental microorganisms which contact the teat over the 8–12 hours between milkings, which organisms might otherwise cause mastitis in the animal.

Other objects and features of the present invention will be apparent to those skilled in the art. The following detailed description of the present invention is intended as a means for illustrating and defining certain preferred embodiments of the present invention and is not intended as a means of limiting, or defining the full scope, of the claimed invention.

DETAILED DESCRIPTION OF THE PRESENT INVENTION

The chemistry of aqueous iodine solutions can be summarized as follows:

$$I_2+H_2O\longleftrightarrow HOI+H^++I- \quad (1)$$

and, $$3I_2+3H_2O\longleftrightarrow IO_3^-+5I^-+6H^+ \quad (2)$$

Molecular iodine ($I_2$), hypoiodous acid (HOI), and iodate ($IO_3^-$) are generally present in the acidic iodine solutions of most commercially-available iodine disinfectants. The acidity is required for maintaining stability in the iodine solutions and for suppressing conversion to other iodine species which are less germicidal. HOI normally exists in very low levels relative to $I_2$, and $IO_3^-$ is an effective oxidant only at pH values less than 4, where significant amounts of $HIO_3$ can exist. Commercial teat dips containing iodine generally have pH values in the range of 3 to 5, which favors a mass action shift in equations (1) and (2), supra, to the left, where $I_2$ exists.

As further background for understanding and practicing the present invention, elemental iodine is only slightly soluble in water (0.03% at 25° C.) Alkali iodines, which combine with iodine to form triiodide ($I_3^-$) increase that solubility. Certain neutral polymers (e.g., polyvinyl pyrrolidone, various polyether glycols) will form loose complexes, termed iodophors, of iodine or triiodide, which serve to increase the solubility of the iodine as well as providing a sustained release reservoir of the iodine. In such solutions, "free" elemental iodine, in equilibrium with complexed iodine, is the basis for the germicidal activity of the formulation. However, as the concentration of iodophor increases in the solution, the free iodine exists in decreasing levels. In dried films, such as From teat dips which have evaporated on cow teats, the free iodine component and, thus, its associated disinfecting capacity, is expected to be minimal.

In order to maintain an appropriate solution pH for the iodophor complexes, such that the free iodine can exist in an optimum disinfecting state (e.g., as shown in equations (1) and (2 ) supra), chemical buffers are included in the compositions of the iodophors. For example, a supplier of iodophor concentrates, West Agro, Inc., suggests the use of citric acid as a buffer when preparing teat dips with their concentrates. Analysis of one such concentrate shows an iodine level of 20.2% and an iodide level of 7.3%, with a pH of approximately 1.7, with the bulk of the remainder being the polymer carrier nonylphenoxy polyoxyethanol (N=12). Two of West Agro, Inc.'s formula recommendations, using this concentrate For preparing effective teat dips, are as follows:

| | | 0.5% iodophor | 1.0% iodophor |
|---|---|---|---|
| 20% Iodophor concentrate | | 2.6% | 5.0% |
| Citric acid | | 0.1% | 0.25% |
| Nonylphenoxy polyoxy-ethanol, N = 12 | | 2.9% | 6.0% |
| Glycerine | | — | 0–10% |
| Alkali | q.s. → pH | 4.8–5.2 | pH 4.5–5.2 |
| Water | | q.s. | q.s. |

The citric acid is used, in combination with the alkali, for providing a buffered pH of approximately 5, which is based on and close to the $Ka_2$, the second ionization constant of citric acid, of 4.76. Other commercial iodophor teat dips have been found to operate in the pH range of 2.8 to 5.5.

Citric acid is a member of a class of organic acids which possesses antimicrobial activity to a varying degree. It has been demonstrated that a significant factor in this cidal activity is the ability of the neutral form of the acid to migrate into the organism across the cell wall, although its ionized form cannot do so. Antimicrobial activity of acids is also related to the total $[H^+]$ concentration present in the environment of the microorganism, which is the reason that such strong organic acids as citric and tartaric acids are used as antimicrobials, e.g., in food where their acidities play a larger role than their inherent ability to act as antimicrobials. Weaker organic acids, such as acetic acid and benzoic acid, which maintain their neutral form to a significant degree in weak pH environments (e.g., pH >5.0), function primarily as antimicrobials on the basis of their inherent structures, rather than as acidifiers.

The range of acids which have been used as antimicrobials includes such small molecules as formic, acetic and propionic acids, as well as a group of so-called alpha-hydroxy acids, such as glycolic, lactic, malic, mandelic, citric and tartaric acids. Other, weaker acids include benzoic, boric, caprylic and the hydrobenzoic acids. Of these, the alpha-hydroxy acid groups contains certain members which have significantly greater inherent antimicrobial activity than citric acid. As indicated earlier, citric acid is used as a buffering agent in the stabilization of iodophor compositions because its second ionization constant lies in the proper range so as to allow citric acid to provide the requisite buffering for these formulations.

Certain weaker members of the alpha-hydroxy acid group have appropriate acid strengths associated with their first ionization constants (i.e., their pKa's) such that they can also perform as buffers for iodophor compositions. These weaker acids, in some cases, are significantly better antimicrobials than citric acid and, thus, can contribute significant additional antimicrobial activity to the iodophor formulations. Since the basis for the cidal activity of organic acids is different than that of iodophors, the combination of the two antimicrobial actions will provide a broader spectrum of microorganism kill for iodophor formulations which contain these cidally-active acid buffering agents.

A further advantage of the use of these antimicrobial acid buffers is that they can remain active for longer time periods, after application of the antimicrobial composition, than the iodophor. The iodine in the iodophor is susceptible to reduction to iodide, as a result of its oxidation of materials in the environment, whereas the organic acids would not be so affected. This resistance to loss in organic environments is the basis for the use of acid preservatives, such as propionic and benzoic acids for food preservation. When the active acid buffers are included in iodophor teat dips, which are designed for providing antimicrobial protection of a cow's udder from one milking to the next, the presence of the residual antimicrobial buffer acid can contribute significantly to that protection long after the cidal effects of the iodophor have worn off. There have been a number of technical publications on the use of iodophor post-milking teat dips, where it has been documented that, while the dips have shown good activity against the contagious microorganisms which infect cows at milking time, they are significantly less effective in protecting the cows against the environmental microorganisms contacted between milkings.

Consistent with the generally-accepted need for an iodophor formulation to be buffered in the 3–5 pH range, the following alpha-hydroxy organic acids, which are better antimicrobials than citric acid, can serve as buffering agents. Their pKa values are also given. For reference purposes, the first pKa of 3.13 for citric acid allows for its use as a buffering agent in the 3.3 pH range, as well as in the 4.76 range cited earlier, based on its second pKa value:

| | |
|---|---|
| Lactic acid | $pK_a = 3.86$ |
| Glycolic acid | $pK_a = 3.83$ |
| Malic acid | $pK_a = 3.40$ |
| Mandelic acid | $pK_a = 3.39$ |

The relative antimicrobial strength of these acids, with respect to citric acid, is: Mandelic acid>Lactic acid>Glycolic acid>Malic acid>Citric acid.

When one of these antimicrobial buffering acids is incorporated into an iodophor teat dip, its tendency to be neutralized by airborne alkaline agents in the farm environment (e.g., ammonia from urine) is less than for the stronger citric acid. The stronger the acid, the greater the tendency for reaction and neutralization. Thus, it is to be expected that these acids would remain in their neutral form for a longer period of time than citric acid and thereby provide extended antimicrobial action. And if one of these antimicrobial acid buffers is incorporated into a barrier-forming iodophor teat dip, the greater quantity of residual acid antimicrobial entrapped in the barrier would provide even greater microbial activity against environmental organisms which can cause mastitis.

It has been found desirable for the organic acid buffer to be in the concentration range of from about 0.05% to 5.0%, typically from about 0.1% to about 3.0% and, preferably, from about 0.2% to 2.0%. In general, the higher amount is used when higher levels of iodophor are present in the composition, such as 2% acid with 2% iodine (in the iodophor), and 0.2% acid with 0.2% iodine. The iodine concentration, preferably in the form of an iodophor, is generally in the range of about 0.5% to 2.0%, typically from about 0.1% to 1.5%, and preferably from about 0.2% to 1.0%. The pH of the teat dips is generally in the range of about 2.8 to 5.5, typically from about 2.8 to 5.0, and preferably from about 3.0 to 4.8.

When it is desired to formulate an antimicrobial-buffered iodophor post-milking teat dip in order to form a protective barrier film around the end of the animal's teat, a suitable polymeric material, from a number of such products known to those skilled in the art, may be chosen to accomplish this purpose. These can be taken from such polymer families as cellulosics and their derivatives, poly(vinyl alcohols) and poly(vinyl acetates), poly(vinylpyrrolidones), poly(acrylamides) and their derivatives (e.g., poly(acrylamidomethansulfonate)), poly(alkyleneglycols), block copolymers of such and their derivatives, e.g., poly(propylene glycol alginate).) The level of inclusion of such materials, on a solids basis, is generally in the range from about 0.2% to 5.0%, typically from 0.5% to about 3.0%, and preferably from about 1.0% to 2.5%. Other materials may be included, as well, which are known to those skilled in the art to be beneficial to the animal's skin, such as humectants and emollients (e.g., glycerin and lanolin derivatives, respectively.)

In the present invention, the antimicrobial-buffered teat dip composition is ordinarily used at a level, such that about 0.5 to about 2.0 grams of the product is applied to each teat end in order to provide the residual antimicrobial action after the cidal effects of the iodine have subsided during the inter-milking period. The higher quantity in this range will correspond to the quantities applied for barrier teat dips, which have higher viscosities (i.e., generally in the range from about 200 to 3,000 centipoise.)

The present invention is illustrated by the following examples. Unless otherwise noted, all parts and percentages in the examples, as well as the instant disclosure and claims, are to be understood as being by weight:

EXAMPLE I

This Example illustrates the use of the present invention in the preparation of a 1% iodine, post-milking teat dip for application to cow udders, where the mandelic-acid buffering agent remaining in the dried glycerin/surfactant film provides protective antimicrobial action between milkings:

| | | |
|---|---|---|
| 20% iodophor concentrate | | 5.00% |
| Mandelic acid | | 0.25% |
| Glycerin (98%) | | 10.00% |
| Igepal CO-720 (alkylphenoxy polyoxyethylene) | | 6.00% |
| Water | | q.s. |
| Sodium hydroxide (1N) | q.s. → pH | 3.4 |

The glycerin, Igepal and mandelic acid are dispensed in sufficient water to achieve about 80% of the final solution weight, and the mixture is stirred until all materials are dissolved, and sufficient water is then added to achieve 95% of the final weight. Thereafter, the alkali is slowly added to raise the pH of the mixture to about 3.4, with a final adjustment being made as the solution weight is brought to 100% of the desired value.

EXAMPLE II

As in Example I, except that malic acid is used in place of mandelic acid, at the 0.25% level.

EXAMPLE III

This Example illustrates the use of the present invention in the preparation of a 0.3% iodine, barrier-forming, post-milking iodophor teat dip for application to the udders of milk-producing mammals. The antimicrobial buffer, mandelic acid, which remains in the protective polymer film barrier that contains the glycerine and surfactant skin conditioners, presents an antimicrobial surface supplementing the physical polymer film which impedes penetration by environmental microorganisms.

| | | |
|---|---|---|
| 20% iodophor concentrate | | 1.5% |
| Mandelic acid | | 0.5% |
| Glycerin (98%) | | 4.00% |
| Igepal CO-720 | | 1.8% |
| Cyanamer N300 LMW (polyacrylamide) | | 2.0% |
| Water | | q.s. |
| Sodium hydroxide (1N) | q.s. → pH | 3.4 |

Stir the Cyanamer into approximately 80% of the required water for 0.5 hours, adding the mandelic acid during the initial stirring. Then, when mixed, sequentially add the glycerin and Igepal, and warm to ambient temperature. Then add the iodophor concentrate and bring to 95% of the final weight with water. This is followed by adding the alkali, with stirring, to adjust to the final pH and dilute to final volume. The viscosity of this product, using a Brookfield Model RVF viscometer, spindle #3 at 2 rpm, is 1,550 centipoise (cps).

EXAMPLE IV

This Example illustrates the use of the present invention in the preparation of a 1% iodine, malic-acid buffered barrier teat dip:

| | | |
|---|---|---|
| 20% iodophor concentrate | | 5.0% |
| Malic acid | | 0.50% |
| Glycerin | | 8.00% |
| Igepal CO-720 | | 6.0% |
| Propylene Glycol Alginate | | 1.0% |
| Water | | q.s. |
| Sodium hydroxide (1N) | q.s. → pH | 3.4 |

To 70% of the required volume of water, add the Igepal and malic acid and warm to 40° C., with stirring to dissolve the materials. Suspend the Alginate in the required amount of glycerine and transfer the mixture to the water, with slight stirring, and bring the mixture weight to 90–95% of the final weight. Cool to ambient temperature and add the alkali to adjust to a pH of approximately 3.4. The viscosity of this product is 2,100 cps.

EXAMPLE V

This Example illustrates the use of the present invention with the antimicrobial lactic acid as a buffer in the preparation of a barrier 0.5% iodophor teat dip incorporating a polyoxyethylene thickener. The latter is a good film-forming material and provides good drip qualities to the dip.

-continued

| | | |
|---|---|---|
| 20% iodophor concentrate | | 2.5% |
| Lactic acid | | 1.42% |
| Glycerin (98%) | | 5.0% |
| Igepal CO-720 | | 3.0% |
| WSR-205 (Polyoxyethylene) | | 2.5% |
| Water | | q.s. |
| Sodium hydroxide (1N) | q.s. → pH | 3.4 |

The WSR-205 is dispersed in the glycerin, then the mixture is added to approximately 85% of the required water and stirred for one hour. The acid is then added and stirred, followed by the Igepal and the iodophor with stirring. The product is brought to approximately 95% of the final weight, adjusted with alkali to the approximate pH, and then to the final weight. The clear, red-brown teat dip has a viscosity of 450 cps.

While only several embodiments of the present invention have been described, it will be obvious to those skilled in the art that many modifications may be made to the present invention without departing from the spirit and scope thereof.

What is claimed is:

1. A composition for improving the anti-microbial activity of mammalian iodophor teat dips, comprising:

an iodophor concentrate; and, an organic acid buffer having an antimicrobial acid within the pKa range of from approximately 2.0 to 6.0, said antimicrobial acid of said organic acid buffer being selected from the group consisting of malic acid, mandelic acid, formic acid, glycolic acid, benzoic acid and a combination thereof.

2. The composition according to claim 1, wherein said antimicrobial acid of said organic acid is within the pKa range of from approximately 3.0 to 5.0.

* * * * *